US010561603B2

(12) United States Patent
Akamine et al.

(10) Patent No.: US 10,561,603 B2
(45) Date of Patent: Feb. 18, 2020

(54) CORE-SHELL STRUCTURE AND TOPICAL AGENT

(71) Applicant: SEKISUI CHEMICAL CO., LTD., Osaka, Osaka (JP)

(72) Inventors: Takayuki Akamine, Osaka (JP); Kazushi Itou, Osaka (JP); Saori Tone, Osaka (JP); Yoshiko Abe, Tokyo (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 0 days.

(21) Appl. No.: 15/740,335

(22) PCT Filed: Jun. 29, 2016

(86) PCT No.: PCT/JP2016/069297
§ 371 (c)(1),
(2) Date: Dec. 27, 2017

(87) PCT Pub. No.: WO2017/002865
PCT Pub. Date: Jan. 5, 2017

(65) Prior Publication Data
US 2018/0185273 A1 Jul. 5, 2018

(30) Foreign Application Priority Data
Jun. 29, 2015 (JP) .................................. 2015-130491

(51) Int. Cl.
*A61K 9/00* (2006.01)
*A61K 31/445* (2006.01)
(Continued)

(52) U.S. Cl.
CPC .............. *A61K 9/0014* (2013.01); *A61K 9/06* (2013.01); *A61K 9/10* (2013.01); *A61K 9/5015* (2013.01);
(Continued)

(58) Field of Classification Search
None
See application file for complete search history.

(56) References Cited

U.S. PATENT DOCUMENTS

2007/0259028 A1 11/2007 Ito
2009/0004281 A1* 1/2009 Nghiem ............... A61K 9/0004
424/490
(Continued)

FOREIGN PATENT DOCUMENTS

CN 101022785 A 8/2007
CN 102946873 A 2/2013
(Continued)

OTHER PUBLICATIONS

Written Opinion of the International Searching Authority (PCT/ISA/237) for Application No. PCT/JP2016/069297 dated Sep. 20, 2016 (English Translation mailed Jan. 11, 2018).
(Continued)

*Primary Examiner* — Aradhana Sasan
(74) *Attorney, Agent, or Firm* — Cheng Law Group, PLLC

(57) ABSTRACT

The present invention provides a core-shell structure having high skin permeability. The core-shell structure includes a core portion containing a hydrophilic drug having a molecular weight of 400 or more; and a shell portion containing a surfactant, and the core portion is a solid, the hydrophilic drug has a water-octanol partition coefficient of −3 or more and 6 or less, the surfactant has an alkyl group or an alkenyl group having 10 to 20 carbon atoms, and a mass ratio between the hydrophilic drug and the surfactant (hydrophilic drug:surfactant) is 1:5 to 1:20.

7 Claims, 6 Drawing Sheets

(51) Int. Cl.
  *A61K 31/53* (2006.01)
  *A61K 9/10* (2006.01)
  *A61K 38/00* (2006.01)
  *A61K 9/06* (2006.01)
  *A61K 9/50* (2006.01)
  *A61K 47/44* (2017.01)
  *A61K 47/14* (2017.01)
(52) U.S. Cl.
  CPC ............ *A61K 31/445* (2013.01); *A61K 31/53* (2013.01); *A61K 38/00* (2013.01); *A61K 47/14* (2013.01); *A61K 47/44* (2013.01)

(56) References Cited

U.S. PATENT DOCUMENTS

| | | | |
|---|---|---|---|
| 2009/0149518 A1* | 6/2009 | Nishii | A61K 31/20 514/367 |
| 2009/0238846 A1 | 9/2009 | Fujii et al. | |
| 2010/0298447 A1 | 11/2010 | Fujii et al. | |
| 2011/0059141 A1 | 3/2011 | Ito | |
| 2013/0165875 A1 | 6/2013 | Choi et al. | |
| 2017/0232106 A1 | 8/2017 | Akamine et al. | |

FOREIGN PATENT DOCUMENTS

| | | |
|---|---|---|
| EP | 2 216 015 A1 | 8/2010 |
| JP | 4843494 B2 | 12/2011 |
| JP | 2014-172840 A | 9/2014 |
| WO | WO-2006/025583 A1 | 3/2006 |
| WO | WO-2007/129427 A1 | 11/2007 |
| WO | WO-2016/043323 A1 | 3/2016 |
| WO | WO-2016/098857 A1 | 6/2016 |

OTHER PUBLICATIONS

International Search Report for the Application No. PCT/JP2016/069297 dated Sep. 20, 2016.

Written Opinion of the International Searching Authority (PCT/ISA/237) for Application No. PCT/JP2016/069297 dated Sep. 20, 2016.

Sugibayashi, Kenji, "Safety concerns of nanomaterials to skin: safety and skin penetration of nanomaterials", Fragrance Journal, 2007, vol. 35, No. 11, pp. 25-28.

Kitaoka, Momoko et al., "Needle-free immunization using a solid-in-oil nanodispersion enhanced by a skin-permeable oligoarginine peptide", International Journal of Pharmaceutics, 2013, vol. 458, pp. 334-339.

The First Office Action for the Application No. 201680026455.8 from The State Intellectual Property Office of the People's Republic of China dated Aug. 14, 2018.

Supplementary European Search Report for the Application No. EP 16 817 973.7 dated Jan. 25, 2019.

European Office Action for the Application No. EP 16 817 973.7 dated Oct. 22, 2019.

\* cited by examiner

[FIG. 1]
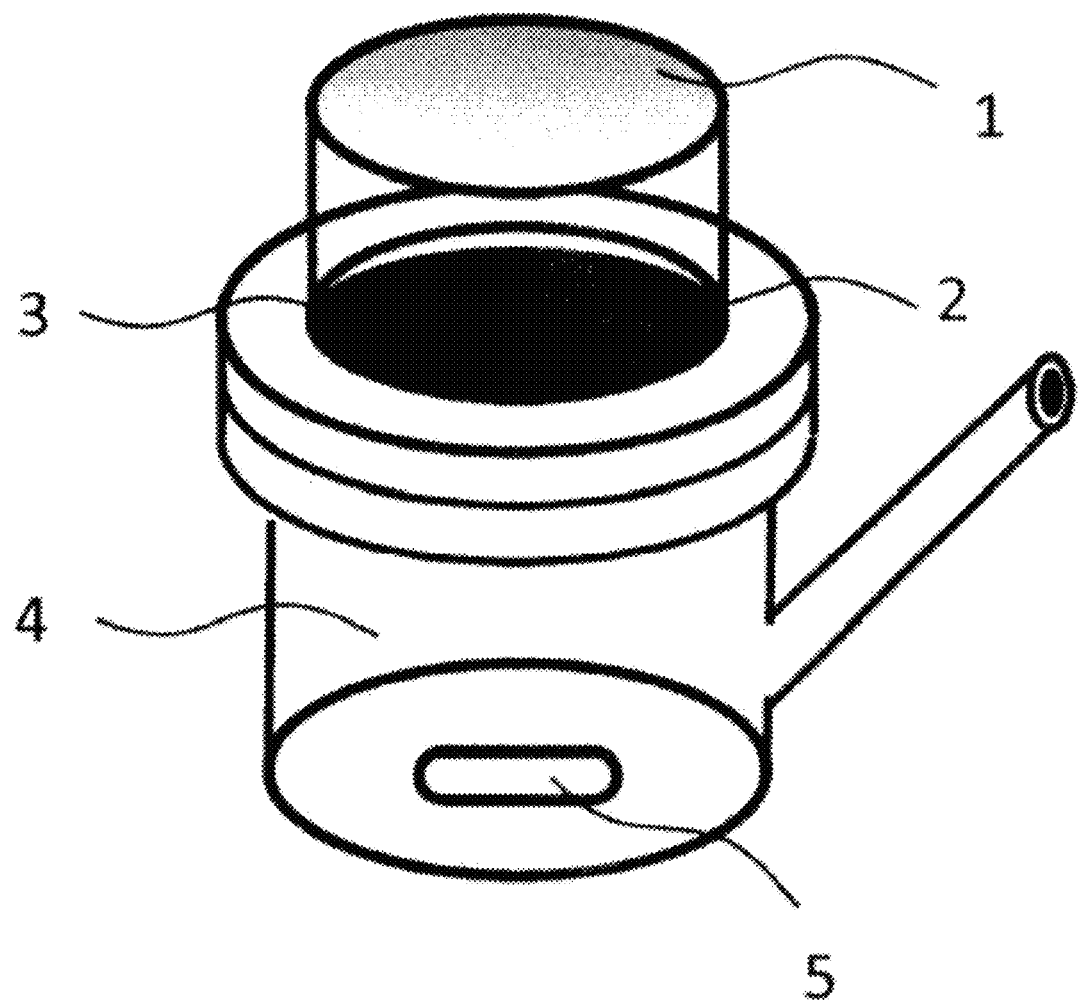

[FIG. 2]
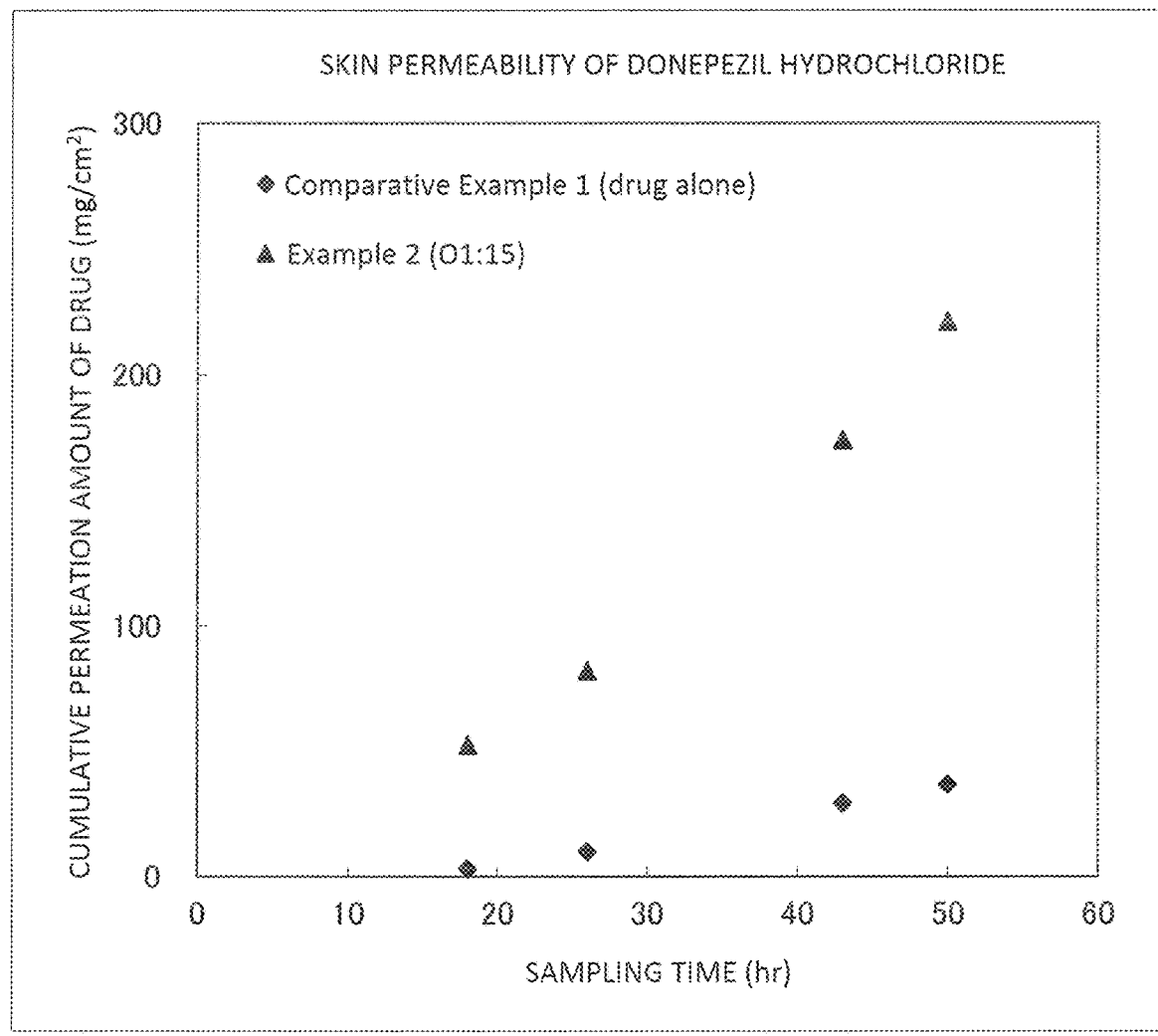

[FIG. 3]
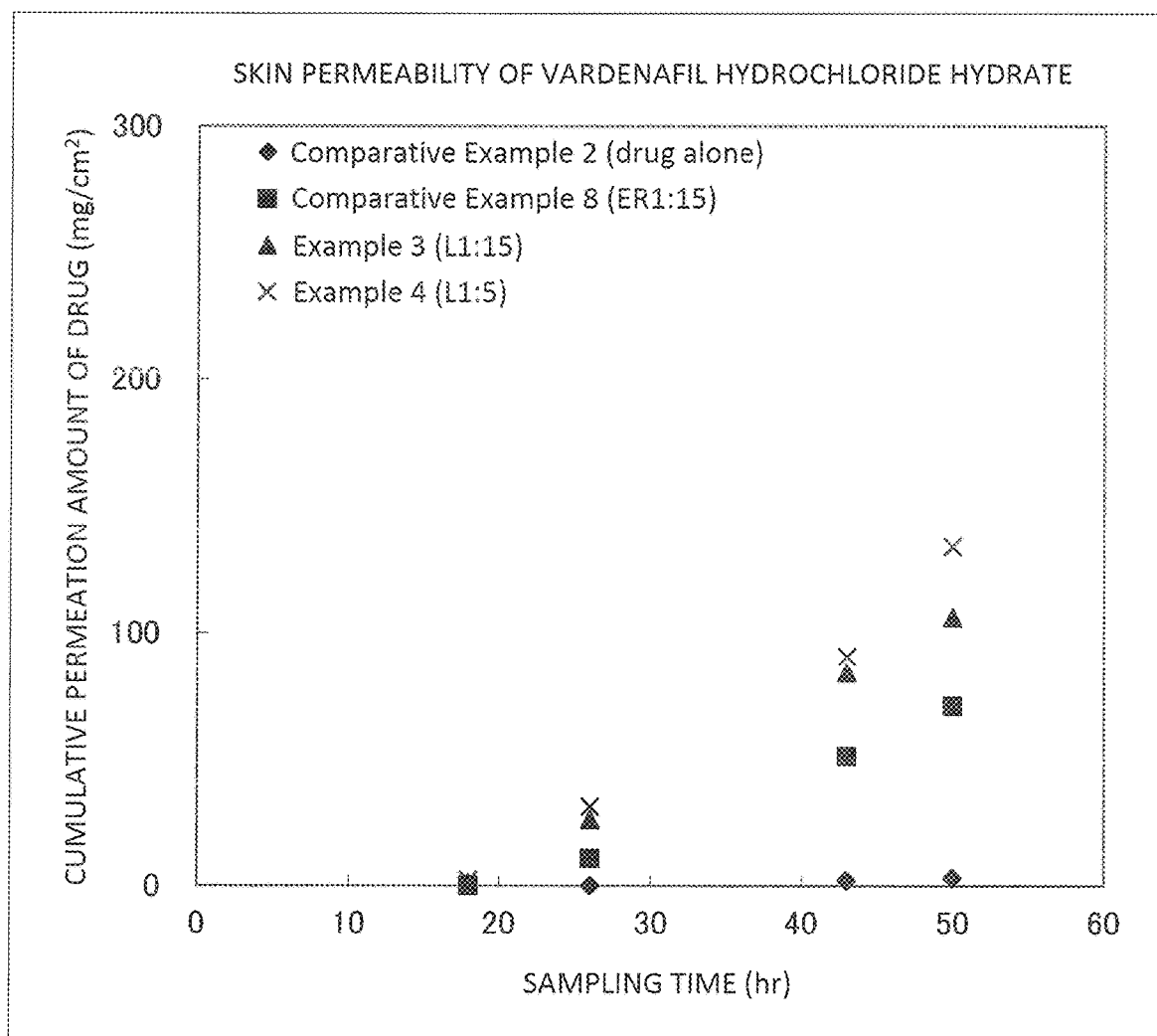

[FIG. 4]
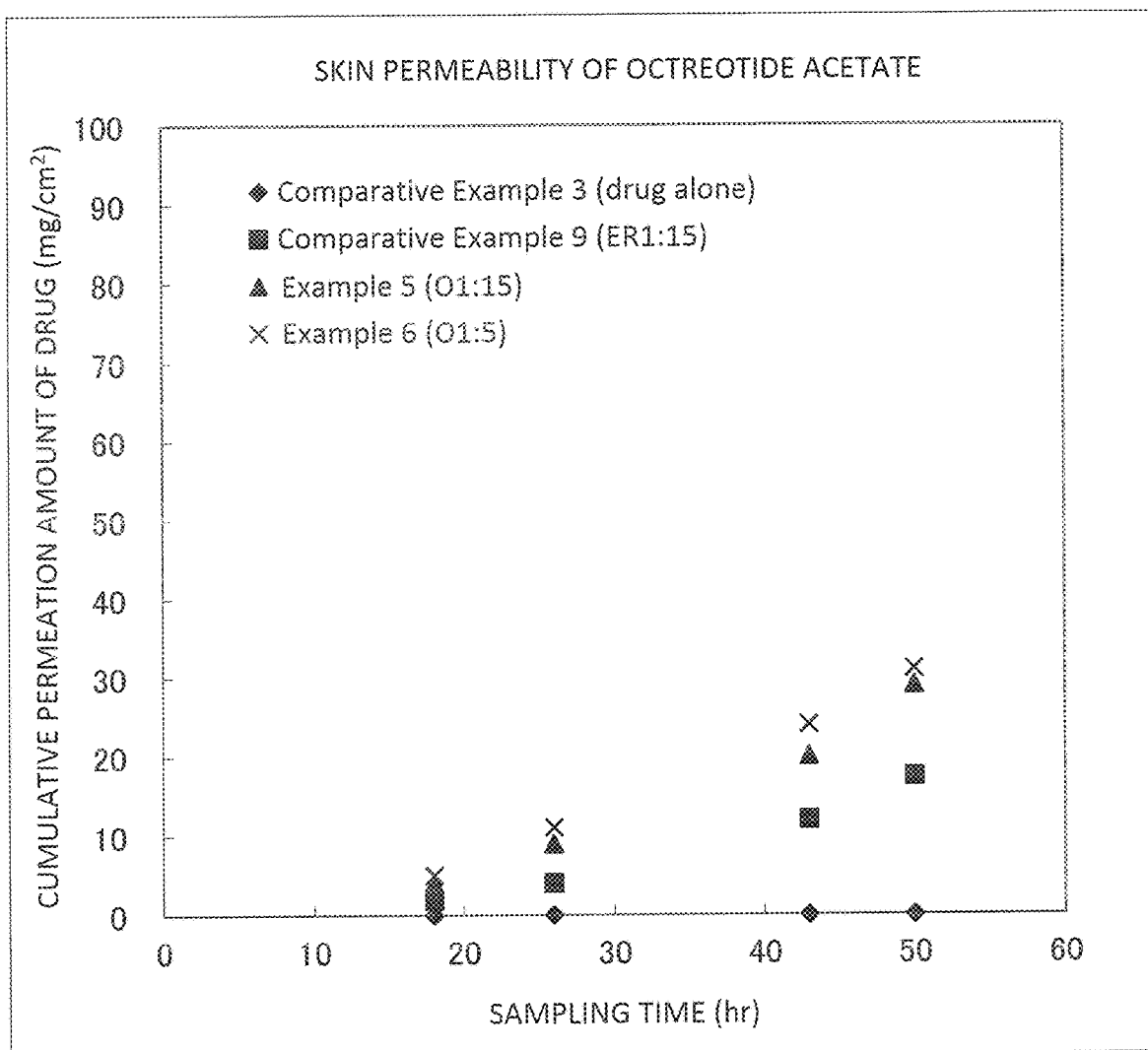

[FIG. 5]
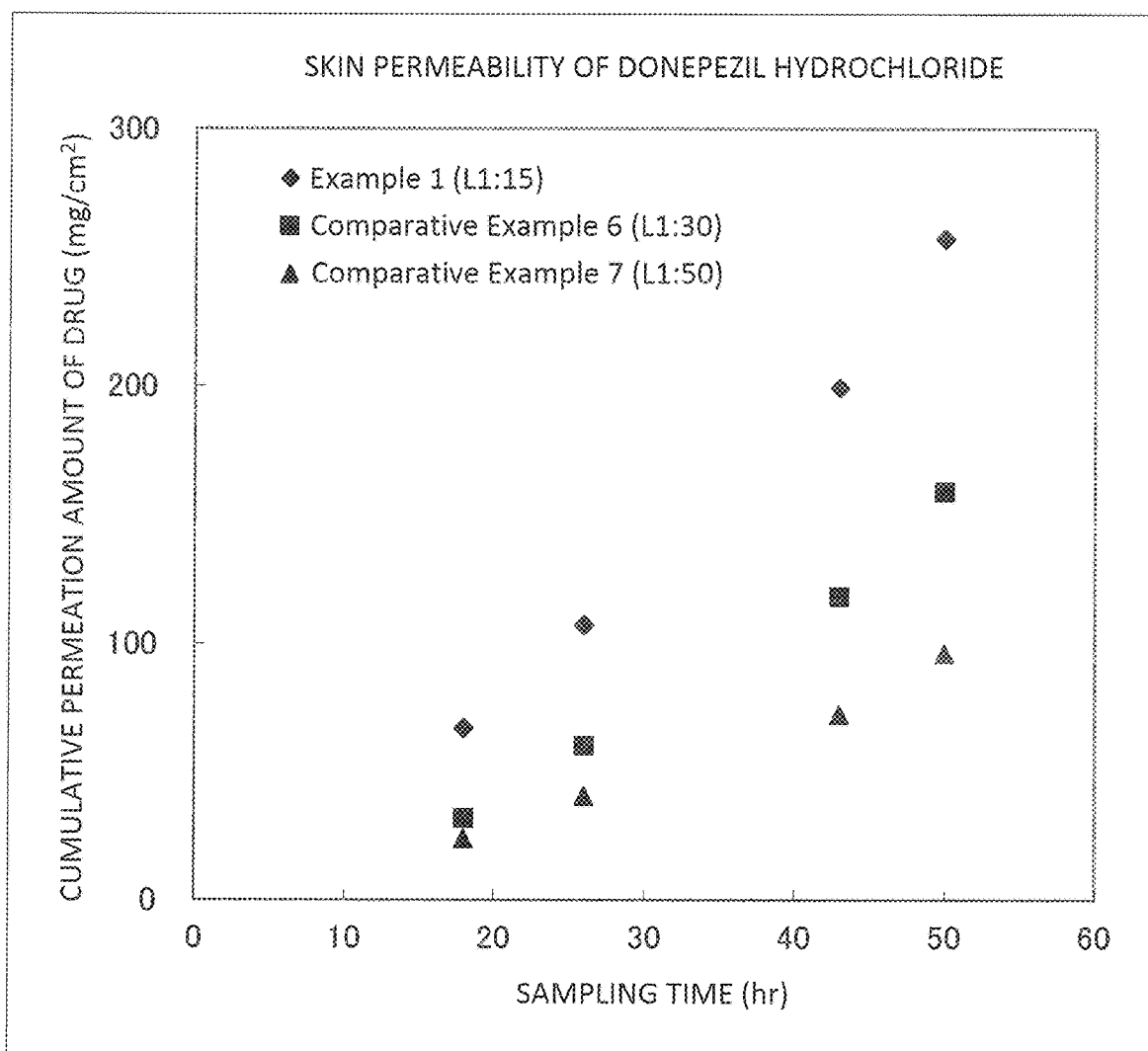

[FIG. 6]
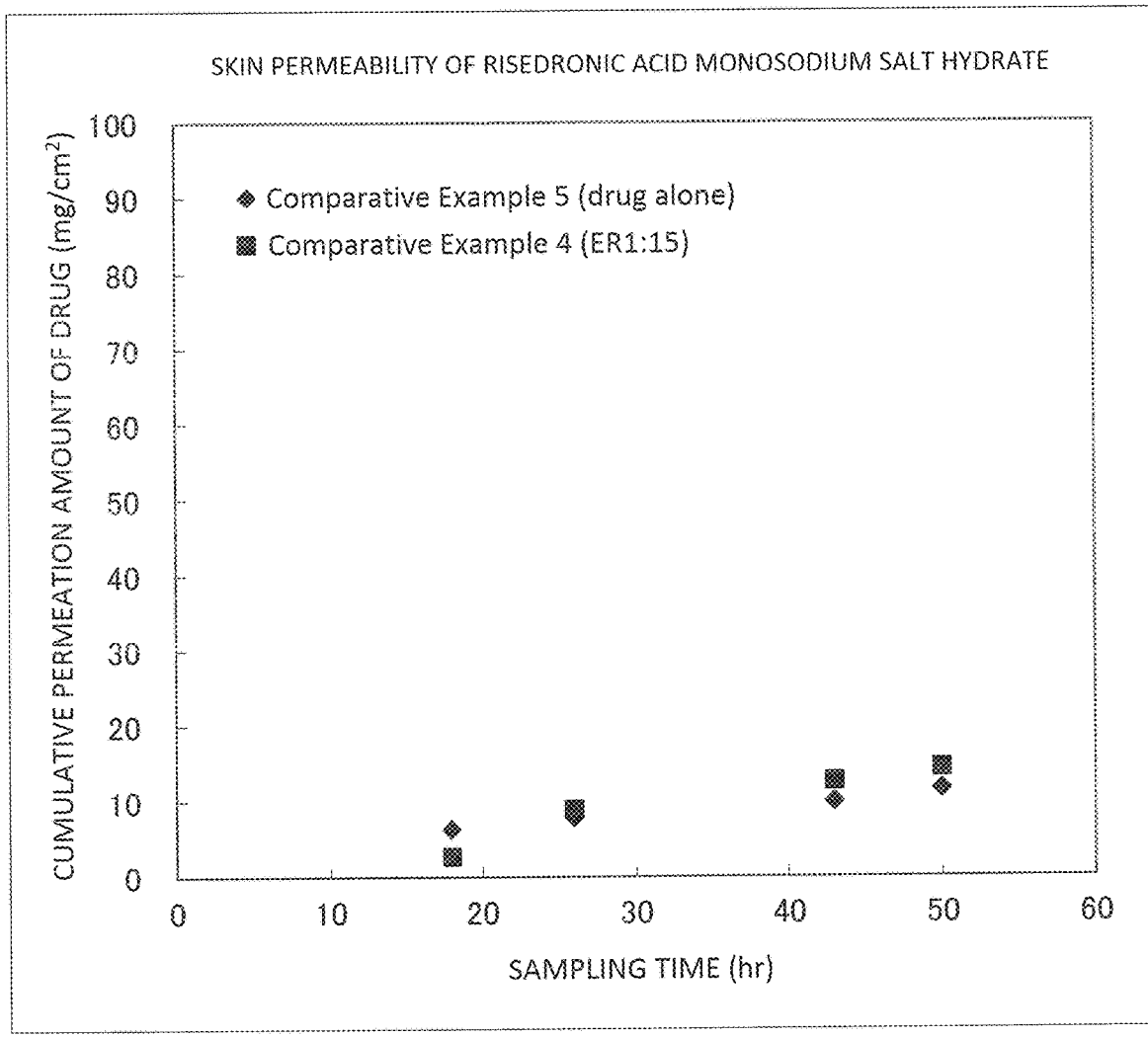

CORE-SHELL STRUCTURE AND TOPICAL AGENT

TECHNICAL FIELD

The present invention relates to a core-shell structure and an external preparation containing the core-shell structure.

BACKGROUND ART

An external preparation in which a drug containing a hydrophilic drug as a principal agent and having been absorbed through skin exhibits systemic action when transferred to the systemic circulation (a systemic action type external preparation) and an external preparation in which a drug absorbed through skin locally shows efficacy (a local action type external preparation) are used.

It is known that a hydrophilic drug having a comparatively low molecular weight in particular tends to be easily permeable through skin in general. Such a hydrophilic drug having a low molecular weight has, however, a problem that although high efficacy can be attained immediately after starting administration, a principal agent contained in the preparation is so early depleted that the efficacy does not last. Therefore, for example, for purposes of long-term administration, a technique for stabilization by changing a specific basic drug to a molecular type has been proposed (Patent Literature 1).

Patent Literature 2 discloses an S/O (Solid-in-Oil) type external preparation in which a drug-containing complex is dissolved or dispersed in an oil phase. It is described that the drug-containing complex is in the form of a solid in which a hydrophilic drug is covered by a surfactant. Patent Literature 2 describes that such an S/O type external preparation is excellent in transdermal absorption.

It is, however, known that a hydrophilic drug having a comparatively high molecular weight tends to be difficult to permeate through skin in general.

CITATION LIST

Patent Literature

Patent Literature 1: International Publication No. WO2007/129427
Patent Literature 2: Japanese Patent No. 4843494

SUMMARY OF INVENTION

Technical Problem

The present inventors focused on a hydrophilic drug particularly having a molecular weight of 400 or more, which is generally regarded to be difficult to permeate through skin among hydrophilic drugs, and conceived to develop a novel formulation technique by which a large amount of such a hydrophilic drug can be caused to permeate through skin. Accordingly, an object of the present invention is to provide a novel core-shell structure having high skin permeability and a systemic or local action type external preparation both using a hydrophilic drug having a molecular weight of 400 or more as a principal agent.

Solution to Problem

The present inventors made earnest studies to solve the above-described problem, and have found that the above-described problem can be solved by utilizing a core-shell structure that includes a specific hydrophilic drug having a molecular weight of 400 or more in a core portion in the form of a solid, and includes a specific surfactant in a shell portion. Specifically, it was found that the core-shell structure having this structure has ability to release a large amount of the hydrophilic drug to be transdermally permeable when applied to skin as a component of an external preparation. The present invention was accomplished through various attempts further made on the basis of this finding, and embraces the following aspects:

Aspect 1. A core-shell structure, including: a core portion containing a hydrophilic drug having a molecular weight of 400 or more; and a shell portion containing a surfactant, and the core portion is a solid, the hydrophilic drug has a water-octanol partition coefficient of −3 or more and 6 or less, the surfactant has an alkyl group or an alkenyl group having 10 to 20 carbon atoms, and a mass ratio between the hydrophilic drug and the surfactant (hydrophilic drug:surfactant) is 1:5 to 1:20.

Aspect 2. The core-shell structure according to aspect 1, in which the surfactant has an alkyl group or an alkenyl group having 10 to 15 carbon atoms and/or an alkenyl group having 16 to 20 carbon atoms.

Aspect 3. The core-shell structure according to aspect 2, in which the surfactant has an alkyl group or an alkenyl group having 10 to 15 carbon atoms.

Aspect 4. The core-shell structure according to any one of aspects 1 to 3, in which the water-octanol partition coefficient of the hydrophilic drug is −3 or more and 4 or less.

Aspect 5. An external preparation, containing the core-shell structure according to any one of aspects 1 to 4.

Advantageous Effects of Invention

The present invention can provide a systemic or local action type external preparation having high skin permeability.

BRIEF DESCRIPTION OF DRAWINGS

FIG. 1 is a schematic diagram of a test cell for skin permeability of a drug used in a test example.
FIG. 2 is a graph illustrating results of Example 2 and Comparative Example 1.
FIG. 3 is a graph illustrating results of Example 3, Example 4, Comparative Example 2 and Comparative Example 8.
FIG. 4 is a graph illustrating results of Example 5, Example 6, Comparative Example 3 and Comparative Example 9.
FIG. 5 is a graph illustrating results of Example 1, Comparative Example 6 and Comparative Example 7.
FIG. 6 is a graph illustrating results of Comparative Examples 4 and 5.

DESCRIPTION OF EMBODIMENT

1. Core-Shell Structure

A core-shell structure of the present invention includes a core portion containing a hydrophilic drug having a molecular weight of 400 or more, and a shell portion containing a surfactant. In other words, in the core-shell structure of the present invention, the core portion contains a hydrophilic drug having a molecular weight of 400 or more, and the shell portion contains a surfactant. The core portion is a solid. The hydrophilic drug has a water-octanol partition coefficient of −3 or more and 6 or less. The surfactant has an alkyl group or an alkenyl group having 10 to 20 carbon atoms. A ratio between the hydrophilic drug and the surfactant (hydrophilic drug:surfactant) is 1:5 to 1:20. Since the core-shell structure of the present invention has the aforementioned structure, the skin permeability of the hydrophilic drug is increased.

The core-shell structure has a structure in which the core portion containing the hydrophilic drug having a molecular weight of 400 or more is coated partially or wholly by the surfactant contained in the shell portion. Incidentally, the core portion and the shell portion may be bound to each other to form an aggregate, and there is no need to cover the whole surface of the core portion by the shell portion. Since the core-shell structure has such a structure, a large amount of the hydrophilic drug contained in the core portion can be caused to permeate when applied to skin.

The shape and the size of the core-shell structure are not particularly limited, and an average size is generally 1 to 10000 nm or 10 to 10000 nm, and a size of 1 to 2000 nm or 50 to 2000 nm is preferred because appropriate transdermal absorption can be easily attained. From the viewpoint that the transdermal absorption is easily attained, the average size is preferably 1 nm to 10000 nm, more preferably 1 nm to 2000 nm, further preferably 2 nm to 500 nm, and particularly preferably 2 nm to 300 nm.

It is noted that the average size of the core-shell structure in the present invention is defined as a number average particle size calculated by a dynamic light scattering method with the core-shell structure dispersed in a solvent (such as a squalane).

1.1. Core Portion

The hydrophilic drug having a molecular weight of 400 or more (hereinafter sometimes simply referred to as the "hydrophilic drug") is not especially limited, and one required for systemic action or local action is usually used.

The core portion is a solid. Since the core portion is a solid, the stability in a base described later is improved. Therefore, when the core-shell structure is dispersed in a base phase as an oil phase, an S/O (Solid in Oil) type external preparation can be formed as described later.

The water-octanol partition coefficient of the hydrophilic drug is −3 or more and 6 or less. Therefore, the skin permeability is increased. From the viewpoint of further improving the skin permeability, the water-octanol partition coefficient is preferably −1 or more, and more preferably 0 or more. Besides, the water-octanol partition coefficient of the hydrophilic drug is preferably 4 or less, and more preferably 1 or less. If the water-octanol partition coefficient of the hydrophilic drug is not more than the upper limit, the skin permeability is further improved.

From the viewpoint of further improving the skin permeability, the hydrophilic drug has a molecular weight of preferably 6,000 or less, more preferably 5,500 or less, further preferably 3,000 or less, and particularly preferably 1,500 or less.

The molecular weight of the hydrophilic drug is preferably 500 or more, more preferably 550 or more, and further preferably 900 or more. If the molecular weight is not less than the lower limit, the shape stability of a particle can be further improved.

Among hydrophilic drugs, a basic drug is not especially limited as long as it is a pharmaceutically acceptable salt, and specific examples include hydrochlorides such as donepezil hydrochloride (molecular weight: 416) and vardenafil hydrochloride hydrate (molecular weight: 579), tartrates such as rivastigmine tartrate (molecular weight: 400), and acetates such as octreotide acetate (molecular weight: 1130) and teriparatide acetate (molecular weight: 4418), and hydrochlorides and acetates are particularly preferred. Besides, specific examples of the acidic drug are not especially limited as long as they are pharmaceutically acceptable salts, and include sodium salts such as bucladesine sodium (molecular weight: 491) and sodium cromoglicate (molecular weight: 512).

The amount of the hydrophilic drug contained in the core-shell structure depends on the type of the hydrophilic drug, and a charged weight of a raw material can be, for example, 0.1 to 30% by mass (based on the total mass of all raw materials contained in the core-shell structure).

The core portion may contain two or more hydrophilic drugs if necessary. In this case, the highly permeable external preparation of the present invention containing the core-shell structure can be used as a combination drug.

The core portion may further contain, in addition to the hydrophilic drug, at least one additional component. The additional component is not especially limited, and examples include a stabilizer, a transdermal absorption promoter, a skin irritation-reducing agent and an antiseptic.

The stabilizer has an effect of stabilizing the core-shell structure, and works to ensure the slow-release effect of the hydrophilic drug by preventing unintended early disintegration of the core-shell structure.

The stabilizer is not especially limited, and specific examples include polysaccharides, proteins and hydrophilic polymer materials. One, two or more of these stabilizers may be contained. The content of the stabilizer in the core portion depends on the type thereof and can be appropriately set, and for example, it may be contained to attain a mass ratio between the hydrophilic drug and the stabilizer of 1:0.1 to 1:10.

The transdermal absorption promoter is not especially limited, and specific examples include higher alcohols, N-acyl sarcosine and a salt thereof, higher monocarboxylic acids, higher monocarboxylic acid esters, aromatic monoterpene fatty acid esters, divalent carboxylic acids having 2 to 10 carbon atoms and salts thereof, polyoxyethylene alkyl ether phosphates and salts thereof, lactic acid, lactic acid esters and citric acid, and the like. One, two or more of these transdermal absorption promoters may be contained. A content of the transdermal absorption promoter in the core portion depends on the type of absorption promoter and may be appropriately set, and it may be contained, for example, to attain a mass ratio between the hydrophilic drug and the transdermal absorption promoter of 1:0.01 to 1:50.

The skin irritation-reducing agent is not especially limited, and specific examples include hydroquinone glycosides, pantethine, tranexamic acid, lecithin, titanium oxide, aluminum hydroxide, sodium nitrite, sodium hydrogen sulfite, soy lecithin, methionine, glycyrrhizic acid, BHT, BHA, vitamin E and derivatives thereof, vitamin C and derivatives thereof, benzotriazole, propyl gallate, and mercaptobenzimidazole. One, two or more of these skin irritation-reducing agents may be contained. A content of the skin irritation-reducing agent in the core portion depends on the type of irritation-reducing agent and may be appropriately set, and it may be contained in a content of, for example, 0.1% by mass to 50% by mass.

The antiseptic is not especially limited, and specific examples include methyl parahydroxybenzoate, propyl parahydroxybenzoate, phenoxyethanol, and thymol. A content of the antiseptic in the core portion depends on the type of antiseptic and may be appropriately set, and it may be contained in a content of, for example, 0.01% by mass to 10% by mass. One, two or more of these antiseptics may be contained.

1.2. Shell Portion

The surfactant is not especially limited as long as it can form the shell portion of the core-shell structure.

The surfactant may be any of a nonionic surfactant, an anionic surfactant, a cationic surfactant and an amphoteric surfactant.

The nonionic surfactant is not especially limited, and examples include fatty acid esters, fatty alcohol ethoxylates, polyoxyethylene alkyl phenyl ethers, alkyl glycosides, fatty acid alkanolamide, polyoxyethylene castor oil and hydrogenated castor oil.

The fatty acid esters are not especially limited but are preferably sugar fatty acid esters. Specific examples include esters of fatty acids, such as erucic acid, oleic acid, lauric acid, stearic acid and behenic acid with sucrose.

Other fatty acid esters are not especially limited, and an example includes an ester of at least one of glycerin, polyglycerin, polyoxyethylene glycerin, sorbitan and polyoxyethylene sorbitol with a fatty acid.

Examples of the anionic surfactants include alkyl sulfate salts, polyoxyethylene alkyl ether sulfate salts, alkyl benzene sulfonate salts, fatty acid salts and phosphate salts.

Examples of the cationic surfactants include alkyl trimethyl ammonium salts, dialkyl dimethyl ammonium salts, alkyl dimethyl benzyl ammonium salts and amine salts.

Examples of the amphoteric surfactants include alkyl amino fatty acid salts, alkyl betaines and alkyl amine oxides.

As the surfactant, sucrose fatty acid esters, glycerin fatty acid esters, polyoxyethylene glycerin fatty acid esters, sorbitan fatty acid esters, polyoxyethylene sorbitol fatty acid esters, polyoxyethylene castor oil and hydrogenated castor oil are particularly preferably used.

Besides, a plurality of surfactants may be used together.

The surfactant has an alkyl group or an alkenyl group having 10 to 20 carbon atoms. Therefore, the skin permeability of the hydrophilic drug is increased. Besides, the surfactant preferably has at least one of an alkyl group or an alkenyl group having 10 to 15 carbon atoms and an alkenyl group having 16 to 20 carbon atoms.

More preferably, the surfactant has an alkyl group or an alkenyl group having 10 to 15 carbon atoms. In this case, the skin permeability of the hydrophilic drug can be further increased.

Examples of the surfactant having an alkyl group or an alkenyl group having 10 to 20 carbon atoms include sucrose oleic acid esters, sucrose lauric acid esters, sucrose palmitic acid esters, sucrose stearic acid esters, glycerin lauric acid esters, glycerin oleic acid esters, glycerin stearic acid esters, sorbitan laurate, sorbitan oleate, sorbitan palmitate and sorbitan stearate. Among these, examples of the surfactant having an alkyl group or an alkenyl group having 10 to 15 carbon atoms include sucrose lauric acid esters, glycerin lauric acid esters and sorbitan laurate. Besides, examples of the surfactant having an alkenyl group having 16 to 20 carbon atoms include sucrose oleic acid esters.

The surfactant is preferably a sucrose fatty acid ester. In particular, from the viewpoint of further increasing the skin permeability of the hydrophilic drug, a sucrose lauric acid ester and/or a sucrose oleic acid ester is preferred, and a sucrose lauric acid ester is more preferred.

The sucrose fatty acid ester may be an ester of sucrose with a saturated fatty acid, or with an unsaturated fatty acid.

A surfactant having a weighted average value of an HLB value of preferably 10 or less, more preferably 5 or less and further preferably 3 or less can be used.

The HLB (Hydrophile Lypophile Balance) value of the present invention can be a parameter used for determining whether an emulsifier is hydrophilic or lipophilic, and takes a value from 0 to 20. A smaller HLB value means stronger lipophilicity. In the present invention, this value is calculated in accordance with the following Griffin equation.

$$\text{HLB value} = 20 \times \{(\text{molecular weight of hydrophilic portion})/(\text{total molecular weight})\}$$

The weighted average value of the HLB value is calculated as follows.

For example, assuming that surfactant materials respectively having HLB values A, B and C are used, and that charged weights thereof in synthesis of the particle are respectively x, y and z, the weighted average value is calculated by a formula: $(xA+yB+zC)\div(x+y+z)$. The surfactant is not especially limited, and can be widely selected from those usable as external preparations.

A mixing amount of the surfactant is set so that a mass ratio between the hydrophilic drug and the surfactant (hydrophilic drug:surfactant) can be 1:5 to 1:20. In this case, the highly permeable systemic or local action type external preparation of the present invention is excellent in the skin permeability.

The shell portion may further contain, in addition to the surfactant, at least one additional component. The additional component is not especially limited, and examples include a skin irritation-reducing agent, an analgesic, a transdermal absorption promoter, a stabilizer and an antiseptic.

The skin irritation-reducing agent is not especially limited, and specific examples include hydroquinone glycosides, pantethine, tranexamic acid, lecithin, titanium oxide, aluminum hydroxide, sodium nitrite, sodium hydrogen sulfite, soy lecithin, methionine, glycyrrhizic acid, BHT, BHA, vitamin E and derivatives thereof, vitamin C and derivatives thereof, benzotriazole, propyl gallate, and mercaptobenzimidazole. One, two or more of these skin irritation-reducing agents may be contained. A content of the skin irritation-reducing agent in the shell portion depends on the type thereof and can be appropriately set, and it can be contained in a content of, for example, 0.1% by mass to 50% by mass.

The analgesic is not especially limited, and specific examples include local anesthetics such as procaine, tetracaine, lidocaine, dibucaine and prilocaine, and salts thereof. One, two or more of the analgesics may be contained. A content of the analgesic in the shell portion depends on the type of analgesic and can be appropriately set, and it may contained in a content of, for example, 0.1% by mass to 30% by mass.

The transdermal absorption promoter is not especially limited, and specific examples include higher alcohols, N-acyl sarcosine and a salt thereof, higher monocarboxylic acids, higher monocarboxylic acid esters, aromatic monoterpene fatty acid esters, divalent carboxylic acids having 2 to 10 carbon atoms and salts thereof, polyoxyethylene alkyl ether phosphates and salts thereof, lactic acid, lactic acid esters and citric acid. One, two or more of these transdermal absorption promoters may be contained. A content of the transdermal absorption promoter in the shell portion depends on the type thereof and can be appropriately set, and it can be contained in a content of, for example, 0.1% by mass to 30% by mass.

The stabilizer has an effect of stabilizing the core-shell structure, and works to ensure the slow-release effect of the hydrophilic drug by preventing unintended early disintegration of the core-shell structure.

The stabilizer is not especially limited, and specific examples include fatty acids and salts thereof, parahydroxybenzoic acid esters such as methylparaben and propylparaben, alcohols such as chlorobutanol, benzyl alcohol and phenyl ethyl alcohol, thimerosal, acetic anhydride, sorbic acid, sodium hydrogen sulfite, L-ascorbic acid, sodium ascorbate, butyl hydroxy anisole, butyl hydroxy toluene, propyl gallate, tocopherol acetate, dl-α-tocopherol, proteins and polysaccharides. One, two or more of the stabilizers may be contained. A content of the stabilizer in the shell portion depends on the type of stabilizer and may be appropriately set, and it can be contained, for example, to attain a mass ratio between the surfactant and the stabilizer of 1:0.01 to 1:50.

The antiseptic is not especially limited, and specific examples include methyl parahydroxybenzoate, propyl parahydroxybenzoate, phenoxyethanol, and thymol. One, two or more of the antiseptics may be contained. A content of the antiseptic in the shell portion depends on the type of antiseptic and may be appropriately set, and it may be contained in a content of, for example, 0.01% by mass to 10% by mass.

1.3. Method for Producing Core-Shell Structure

The core-shell structure can be produced by a method including, for example, a step of drying a W/O emulsion containing an active ingredient in an aqueous phase.

The W/O emulsion is not especially limited as long as it is what is called a water-in-oil emulsion, specifically, an emulsion in which a droplet of an aqueous solvent is dispersed in an oil solvent.

The W/O emulsion containing the active ingredient in the aqueous phase can be obtained by mixing an aqueous solvent, such as water or a buffer aqueous solution, containing the active ingredient with an oil solvent, such as cyclohexane, hexane or toluene, containing the surfactant. The aqueous solvent containing the active ingredient may contain, in addition to the active ingredient, an additive component such as a stabilizer, an absorption promoter or a stimulation reducing agent if necessary. Besides, also the oil solvent containing the surfactant may contain, in addition to the surfactant, an additive component such as a stimulation reducing agent, an analgesic, an absorption promoter or a stabilizer if necessary. A method for mixing is not especially limited as long as the W/O emulsion can be formed, and for example, stirring with a homogenizer or the like can be employed.

A condition for the stirring with a homogenizer is, for example, about 5000 to 50000 rpm, and more preferably about 10000 to 30000 rpm.

A mass ratio, in the W/O emulsion, of the surfactant to the active ingredient (surfactant/active ingredient) is not especially limited, and is, for example, 2 to 100, preferably 3 to 50, and more preferably 5 to 30.

A method for drying the W/O emulsion containing the active ingredient in the aqueous phase is not especially limited as long as the solvents (the aqueous solvent and the oil solvent) contained in the emulsion can be removed, and examples include freeze drying and drying under reduced pressure, and the freeze drying is preferably employed.

Besides, from the viewpoint of further reducing the number average particle size of the resultant core-shell structure, a step of subjecting, to a heat treatment, the W/O emulsion containing the active ingredient in the aqueous phase or a dried product of the W/O emulsion is preferably further included. A heat treatment temperature is, for example, 30 to 60° C., preferably 35 to 50° C. and more preferably 35 to 45° C.

A heat treatment time is appropriately adjusted in accordance with the heat treatment temperature, and is, for example, 1 to 30 days, preferably 2 to 15 days, and more preferably 3 to 7 days. Incidentally, if the W/O emulsion is subjected to the heat treatment, the above-described drying is performed after the treatment, and thus, the core-shell structure of the present invention can be obtained.

Alternatively, as another method for further reducing the number average particle size of the resultant core-shell structure, a method in which filtration with a filter or the like is performed or centrifugation is performed after dispersing, in a solvent or the like, the W/O emulsion containing the active ingredient in the aqueous phase or the dried product of the W/O emulsion if necessary. A filter pore size in employing the filter filtration is, for example, 1 μm or less, preferably 0.2 μm or less, and more preferably 0.1 μm or less.

The core-shell structure of the present invention may be used as it is, or may be dispersed in a base phase or the like described below before use.

1.4. Base Phase

The highly permeable systemic or local action type external preparation of the present invention may further contain a phase containing a base (a base phase), with the core-shell structure contained in the base phase. In this case, the core-shell structure is dispersed or dissolved in the base phase.

The base is not especially limited, and can be selected from a wide range of bases usable for an external preparation.

As described above, the core portion is a solid in the core-shell structure of the present invention. Therefore, if the base phase is an oil phase, an S/O (Solid in Oil) type external preparation can be formed by dispersing the core-shell structure in the oil phase of the base phase. The S/O type external preparation can be obtained by, for example, dispersing or dissolving the core-shell structure obtained by the above-described production method in the oil phase.

The base is not especially limited, and can be appropriately selected in accordance with the intended use from bases suitable for dispersing or dissolving the core-shell structure.

Besides, a plurality of bases may be used together.

The base is not especially limited, and examples include vegetable oils, animal oils, neutral lipids, synthetic fats and oils, sterol derivatives, waxes, hydrocarbons, monoalcohol carboxylic acid esters, hydroxy acid esters, polyhydric alcohol fatty acid esters, silicones, higher (polyhydric) alcohols, higher fatty acids and fluorine-based oils.

The vegetable oils are not especially limited, and examples include soy oil, sesame oil, olive oil, coconut oil, balm oil, rice oil, cotton seed oil, sunflower oil, rice bran oil, cacao butter, cone oil, safflower oil and rapeseed oil.

The animal oils are not especially limited, and examples include mink oil, turtle oil, fish oil, cow oil, horse oil, pig oil and shark squalane.

The natural lipids are not especially limited, and examples include triolein, trilinolein, trimyristin, tristearin and triarachidonin.

The synthetic fats and oils are not especially limited, and examples include phospholipid and azone.

The sterol derivatives are not especially limited, and examples include dihydrocholesterol, lanosterol, dihydrolanosterol, fitosterol, cholic acid and cholesterol linoleate.

Examples of the waxes include candelilla wax, carnauba wax, rice wax, Japan wax, beeswax, montan wax, ozokerite, ceresin, paraffin wax, microcrystalline wax, petrolatum, Fischer-Tropsch wax, polyethylene wax and an ethylene-propylene copolymer.

Examples of the hydrocarbons include liquid paraffin (mineral oil), heavy liquid isoparaffin, light liquid isoparaffin, α-olefin oligomer, polyisobutene, hydrogenated polyisobutene, polybutene, squalane, olive-derived squalane, squalene, vaseline and solid paraffin.

Examples of the monoalcohol carboxylic acid esters include octyldodecyl myristate, hexyldecyl myristate, octyldodecyl isostearate, cetyl palmitate, octyldodecyl palmitate, cetyl octoate, hexyldecyl octoate, isotridecyl isononanoate, isononyl isononanoate, octyl isononanoate, isotridecyl isononanoate, isodecyl neopentanoate, isotridecyl neopentanoate, isostearyl neopentanoate, octyldodecyl neodecanoate, oleyl oleate, octyldodecyl oleate, octyldodecyl ricinoleate, octyldodecyl lanolate, hexyldecyl dimethyloctanoate, octyldodecyl erucate, hydrogenated castor oil isostearate, ethyl oleate, ethyl avocado oil fatty acid, isopropyl myristate, isopropyl palmitate, octyl palmitate, isopropyl isostearate, isopropyl lanolate, diethyl sebacate, diisopropyl sebacate, dioctyl sebacate, diisopropyl adipate, dibutyl octyl sebacate, diisobutyl adipate, dioctyl succinate and triethyl citrate.

Examples of the hydroxy acid esters include cetyl lactate, diisotearyl malate and hydrogenated castor oil monoisostearate.

Examples of the polyhydric alcohol fatty acid esters include glyceryl trioctanoate, glyceryl trioleate, glyceryl triisostearate, glyceryl diisostearate, glyceryl tri(caprylate/caprate), glyceryl tri(caprylate/caprate/myristate/stearate), hydrogenated rosin triglyceride (hydrogenated ester gum), rosin triglyceride (ester gum), glyceryl behenate eicosadioate, trimethylolpropane trioctanoate, trimethylolpropane triisostearate, neopentyl glycol dioctanoate, neopentyl glycol dicaprate, 2-butyl-2-ethyl-1,3-propanediol dioctanoate, propylene glycol dioleate, pentaerythrityl tetraoctanoate, hydrogenated rosin pentaerythrityl, ditrimethylolpropane triethylhexanoate, ditrimethylolpropane (isostearate/sebacate), pentaerythrityl triethylhexanoate, dipentaerythrityl (hydroxystearate/stearate/rosinate), diglyceryl diisostearate, polyglyceryl tetraisostearate, polyglyceryl-10 nonaisostearate, polyglyceryl-8 deca(erucate/isostearate/ricinoleate), diglyceryl oligoester (hexyldecanoate/sebacate), glycol distearate (ethylene glycol distearate), 3-methyl-1,5-pentanediol dineopentanoate and 2,4-diethyl-1,5-pentanediol dineopentanoate.

Examples of the silicones include dimethicone (dimethylpolysiloxane), highly polymerized dimethicone (highly polymerized dimethylpolysiloxane), cyclomethicone (cyclic dimethylsiloxane, decamethylcyclopentasiloxane), phenyl trimethicone, diphenyl dimethicone, phenyl dimethicone, stearoxypropyl dimethyl amine, (aminoethyl aminopropyl methicone/dimethicone) copolymer, dimethiconol, dimethiconol crosspolymer, silicone resin, silicone rubber, amino-modified silicone such as aminopropyl dimethicone or amodimethicone, cation-modified silicone, polyether-modified silicone such as dimethicone copolyol, polyglycerin-modified silicone, sugar-modified silicone, carboxylic acid-modified silicone, phosphoric acid-modified silicone, sulfuric acid-modified silicone, alkyl-modified silicone, fatty acid-modified silicone, alkyl ether-modified silicone, amino acid-modified silicone, peptide-modified silicone, fluorine-modified silicone, cation-modified or polyether-modified silicone, amino-modified or polyether-modified silicone, alkyl-modified or polyether-modified silicone, and polysiloxane-oxyalkylene copolymer.

Examples of the higher (polyhydric) alcohols include cetanol, myristyl alcohol, oleyl alcohol, lauryl alcohol, cetostearyl alcohol, stearyl alcohol, aralkyl alcohol, behenyl alcohol, jojoba alcohol, chimyl alcohol, selachyl alcohol, batyl alcohol, hexyldecanol, isostearyl alcohol, 2-octyl dodecanol and dimer diol.

Examples of the higher fatty acids include lauryl acid, myristic acid, palmitic acid, stearic acid, isostearic acid, behenic acid, undecylenic acid, 12-hydroxystearic acid, palmitoleic acid, oleic acid, linolic acid, linolenic acid, erucic acid, docosahexaenoic acid, eicosapentaenoic acid, isohexadecanoic acid, anteiso-heneicosanoic acid, long-chain branched fatty acid, dimer acid and hydrogenated dimer acid.

Examples of the fluorine-based oils include perfluorodecane, perfluorooctane and perfluoropolyether.

Other examples of the second base are not especially limited, but include bases used in ointments, creams, aerosols, tapes, patches, poultices, gels and microneedles.

2. Composition of Highly Permeable Systemic or Local Action Type External Preparation The highly permeable systemic or local action type external preparation of the present invention contains at least the above-described core-shell structure.

The highly permeable systemic or local action type external preparation of the present invention may further contain other additive components in accordance with the dosage form, intended use and the like.

The additive components are not especially limited, and examples include an excipient, a colorant, a lubricant, a binder, an emulsifier, a thickener, a humectant, a stabilizer, a preservative, a solvent, a solubilizer, a suspending agent, a buffer, a pH adjuster, a gelling agent, an adhesive, an antioxidant, a transdermal absorption promoter, a stimulation reducing agent, an antiseptic, a chelating agent and a dispersant.

Besides, in the highly permeable systemic or local action type external preparation of the present invention, the core-shell structure may be dispersed, if the base phase is not contained, or the base phase containing the core-shell structure (hereinafter both of which are sometimes generically designated as the "core-shell structure-containing basic component") may be dispersed, if the base phase is contained, in another component. In this case, the highly permeable systemic or local action type external preparation of the present invention is offered with the core-shell structure-containing basic component mixed and dispersed in or emulsified with a component that does not completely dissolve the core-shell structure-containing basic component. In order to offer the external preparation as, but not especially limited to, for example, an ointment, a cream, an aerosol, a tape, a patch, a poultice, a gel or a microneedle, the core-shell structure-containing basic component can be mixed and dispersed in or emulsified with a base appropriately selected in accordance with the dosage form such as bases used in the above-described dosage forms.

3. Method for Producing Highly Permeable Systemic or Local Action Type External Preparation Although this is not restrictive, the highly permeable systemic or local action type external preparation of the present invention can be produced, for example, as follows.

First, although this is not restrictive, the core-shell structure of the present invention can be produced, for example, as follows: A drug and if desired, an additive component such as a stabilizer, a transdermal absorption promoter or a skin-irritation reducing agent are dissolved in pure water or a solvent such as a phosphate buffer. To the resultant, a solution obtained by dissolving, in a solvent such as cyclohexane, hexane or toluene, a surfactant and, if desired, an additive component such as a skin-irritation reducing agent, an analgesic, a transdermal absorption promoter or a stabilizer is added, followed by stirring with a homogenizer. Thereafter, the resultant is freeze dried, and thus, the core-shell structure of the present invention can be prepared.

The core-shell structure can be used to produce a persistent systemic or local action type external preparation by, for example, a solution coating method. In the solution coating method, not only the core-shell structure of the present invention and the base but also, if desired, an additive component such as a transdermal absorption promoter, a thickener or a gelling agent are added in a prescribed ratio to a solvent such as hexane, toluene or ethyl acetate, and the resultant is stirred to prepare a homogeneous solution. A solid component concentration in the solution is preferably 10 to 80% by mass, and more preferably 20 to 60% by mass.

Next, the solution containing the above-described components is uniformly applied on a release liner (such as a silicone-treated polyester film) using a coater such as a knife coater, a comma coater or a reverse coater, the resultant is dried to complete a drug-containing layer, and a support is laminated on the layer to obtain a transdermal absorption type formulation. Depending on the type of support, a release liner may be laminated on the surface of the layer after forming the layer on the support.

As another method, for example, the core-shell structure is mixed with, if necessary, a base and an additive component such as a transdermal absorption promoter, a stabilizer, a thickener and a gelling agent, and the resultant is used, in accordance with the intended use, in a state where it is stacked on or impregnated into a natural fabric member such as gauze or absorbent cotton, a synthetic fiber fabric member such as polyester or polyethylene, a woven fabric or nonwoven fabric obtained by appropriately combining these members, or a transparent film, so as to be held thereon, with the resultant covered by an adhesive covering member or the like.

The transdermal absorption type formulation thus obtained is appropriately cut, in accordance with the intended use, into an elliptical, circular, square or rectangular shape. Besides, an adhesive layer or the like may be provided in a surrounding portion if necessary.

4. Use of Highly Permeable Systemic or Local Action Type External Preparation

Although this is not restrictive, the highly permeable systemic or local action type external formulation of the present invention is generally persistent for one day to one week, and in a preferred aspect, it is used to be applied once in a period of one day to one week.

The target disease depends on the type of a salt form hydrophilic drug.

Although this is not restrictive, the highly permeable systemic or local action type external formulation of the present invention is used as a tape (of reservoir type, matrix type or the like), an ointment, a lotion, an aerosol, a plaster, an aqueous poultice, a cream, a gel, an aerosol, a patch or a microneedle.

EXAMPLES

Now, the present invention will be described in detail with reference to examples and a test example, and it is noted that the present invention is not limited to these examples.

Example 1

First, 0.2 g of donepezil hydrochloride (manufactured by Tokyo Chemical Industry Co., Ltd., molecular weight: 416, water-octanol partition coefficient: 4.3) was dissolved in 40 g of pure water, and a solution obtained by dissolving 3.0 g of sucrose lauric acid ester (L-195, manufactured by Mitsubishi-Kagaku Foods Corporation; HLB value: 1) in 80 g of cyclohexane was added to the resultant, followed by stirring with a homogenizer (25,000 rpm, 2 minutes). The resultant was freeze dried for 2 days to obtain a core-shell structure. Besides, a number average particle size calculated by the dynamic light scattering method (Zetasizer Nano S, manufactured by Spectris Co., Ltd.) after dispersing the core-shell structure in Olive Squalane (manufactured by Nikko Chemicals Co., Ltd.) was 211 nm. To 1.0 g of the thus obtained core-shell structure, 2.0 g of Plastibase (manufactured by Taisho Pharmaceutical Co., Ltd., the Japanese Pharmacopoeia) was added to be mixed and dispersed to prepare an S/O type external preparation.

Example 2

An S/O type external preparation was prepared in the same manner as in Example 1 except that sucrose lauric acid ester used in Example 1 was replaced with sucrose oleic acid ester (O-170, manufactured by Mitsubishi-Kagaku Foods Corporation; HLB value: 1). Besides, a number average particle size calculated by the dynamic light scattering method (Zetasizer Nano S, manufactured by Spectris Co., Ltd.) after dispersing the core-shell structure in Olive Squalane (manufactured by Nikko Chemicals Co., Ltd.) was 23 nm.

Example 3

An S/O type external preparation was prepared in the same manner as in Example 1 except that donepezil hydrochloride used in Example 1 was replaced with vardenafil hydrochloride trihydrate (manufactured by Atomax Chemicals Co., Ltd., molecular weight: 579, water-octanol partition coefficient: 3.2). Besides, a number average particle size calculated by the dynamic light scattering method (Zetasizer Nano S, manufactured by Spectris Co., Ltd.) after dispersing the core-shell structure in Olive Squalane (manufactured by Nikko Chemicals Co., Ltd.) was 153 nm.

Example 4

An S/O type external preparation was prepared in the same manner as in Example 3 except that the amount of sucrose lauric acid ester of Example 3 was changed to 1.0 g. Besides, a number average particle size calculated by the dynamic light scattering method (Zetasizer Nano S, manufactured by Spectris Co., Ltd.) after dispersing the core-shell structure in Olive Squalane (manufactured by Nikko Chemicals Co., Ltd.) was 207 nm.

Example 5

An S/O type external preparation was prepared in the same manner as in Example 1 except that donepezil hydrochloride used in Example 1 was replaced with octreotide acetate (manufactured by BACHE, molecular weight: 1139, water-octanol partition coefficient: 0.1) and that sucrose lauric acid ester used in Example 1 was replaced with sucrose oleic acid ester (0-170, manufactured by Mitsubishi-Kagaku Foods Corporation; HLB value: 1). Besides, a number average particle size calculated by the dynamic light scattering method (Zetasizer Nano S, manufactured by Spectris Co., Ltd.) after dispersing the core-shell structure in Olive Squalane (manufactured by Nikko Chemicals Co., Ltd.) was 262 nm.

Example 6

An S/O type external preparation was prepared in the same manner as in Example 5 except that the amount of sucrose oleic acid ester of Example 5 was changed to 1.0 g. Besides, a number average particle size calculated by the dynamic light scattering method (Zetasizer Nano S, manufactured by Spectris Co., Ltd.) after dispersing the core-shell structure in Olive Squalane (manufactured by Nikko Chemicals Co., Ltd.) was 298 nm.

Comparative Example 1

An external preparation was prepared by adding 62.5 mg of donepezil hydrochloride to 3.0 g of Plastibase to be mixed and dispersed therein.

Comparative Example 2

An external preparation was prepared by adding 62.5 mg of vardenafil hydrochloride trihydrate to 3.0 g of Plastibase to be mixed and dispersed therein.

Comparative Example 3

An external preparation was prepared by adding 62.5 mg of octreotide acetate to 3.0 g of Plastibase to be mixed and dispersed therein.

Comparative Example 4

An S/O type external preparation was prepared in the same manner as in Example 1 except that donepezil hydrochloride used in Example 1 was replaced with risedronic acid monosodium salt hemipentahydrate (manufactured by Tokyo Chemical Industry Co., Ltd., molecular weight: 306, water-octanol partition coefficient: −5.0) and that sucrose lauric acid ester used in Example 1 was replaced with sucrose erucic acid ester (ER-290, manufactured by Mitsubishi-Kagaku Foods Corporation; HLB value: 2). Besides, a number average particle size calculated by the dynamic light scattering method (Zetasizer Nano S, manufactured by Spectris Co., Ltd.) after dispersing the core-shell structure in Olive Squalane (manufactured by Nikko Chemicals Co., Ltd.) was 196 nm.

Comparative Example 5

An external preparation was prepared by adding 62.5 mg of risedronic acid monosodium salt hemipentahydrate to 3.0 g of Plastibase to be mixed and dispersed therein.

Comparative Example 6

An S/O type external preparation was prepared in the same manner as in Example 1 except that the amount of donepezil hydrochloride of Example 1 was changed to 0.1 g. Besides, a number average particle size calculated by the dynamic light scattering method (Zetasizer Nano S, manufactured by Spectris Co., Ltd.) after dispersing the core-shell structure in Olive Squalane (manufactured by Nikko Chemicals Co., Ltd.) was 3 nm.

Comparative Example 7

An S/O type external preparation was prepared in the same manner as in Example 1 except that the amount of donepezil hydrochloride of Example 1 was changed to 0.06 g. Besides, a number average particle size calculated by the dynamic light scattering method (Zetasizer Nano S, manufactured by Spectris Co., Ltd.) after dispersing the core-shell structure in Olive Squalane (manufactured by Nikko Chemicals Co., Ltd.) was 3 nm.

Comparative Example 8

An S/O type external preparation was prepared in the same manner as in Comparative Example 4 except that risedronic acid monosodium salt hemipentahydrate used in Comparative Example 4 was replaced with vardenafil hydrochloride trihydrate (manufactured by Atomax Chemicals Co., Ltd., molecular weight: 579, water-octanol partition coefficient: 3.2). Besides, a number average particle size calculated by the dynamic light scattering method (Zetasizer Nano S, manufactured by Spectris Co., Ltd.) after dispersing the core-shell structure in Olive Squalane (manufactured by Nikko Chemicals Co., Ltd.) was 9 nm.

Comparative Example 9

An S/O type external preparation was prepared in the same manner as in Comparative Example 4 except that risedronic acid monosodium salt hemipentahydrate used in Comparative Example 4 was replaced with octreotide acetate (manufactured by BACHE, molecular weight: 1139, water-octanol partition coefficient: 0.1). Besides, a number average particle size calculated by the dynamic light scattering method (Zetasizer Nano S, manufactured by Spectris Co., Ltd.) after dispersing the core-shell structure in Olive Squalane (manufactured by Nikko Chemicals Co., Ltd.) was 247 nm.

Test Example 1: Skin Permeability Test in Hairless Rat

Skin of a hairless rat (Japan SLC, Inc., taken out from 8-week-old HWY/Sic) was set in a test cell for skin permeability of a drug (FIG. 1). In an upper portion of this device, 330 mg of each of the various external preparations produced in Examples 1, 2, 3 and 5 and Comparative Examples 1, 2, 3, 4, 5, 8 and 9, 125 mg of each of the external preparations of Examples 4 and 6, 640 mg of the external preparation of Comparative Example 6, or 1050 mg (about 3 cm$^2$) of the external preparation of Comparative Example 7 was applied, and a lower receptor layer was charged with a buffer, which had been obtained by adjusting, with NaOH, to pH 7.2 of a liquid containing, in distilled water, $5 \times 10^{-4}$ M of $NaH_2PO_4$, $2 \times 10^{-4}$ M of $Na_2HPO_4$, $1.5 \times 10^{-4}$ M of NaCl and 10 ppm of gentamicin sulfate (G1658, manufactured by Wako Pure Chemical Industries, Ltd.), and the resultant device was set in a thermostatic chamber kept at 32° C. from the start of the test. A prescribed time after starting the test, 1 ml of the liquid held in the lower receptor layer in the chamber was collected, and immediately, 1 ml of a liquid having the same composition was replenished. Methanol was added to each receptor liquid sample thus collected to extract eluted lipid and the like followed by centrifugation, and thereafter, the concentration of the drug in the supernatant was quantitatively determined by high performance liquid chromatography (HPLC) (Apparatus: System controller: CBM-20A, manufactured by Shimadzu Corporation, Feeding unit: LC-20AD, manufactured by Shimadzu Corporation, Column oven: CTO-20A, manufactured by Shimadzu Corporation, Detector: SPD-20A, manufactured by Shimadzu Corporation, Detection wavelength: 271 nm, Column: Hypersi GOLD, manufactured by Thermo Scientific, 150×4.6 mm, 3 μm). The results of a cumulative permeation amount (mg/cm$^2$) of each drug exhibiting the skin permeability are shown in Table 1 and FIGS. 2 to 6.

TABLE 1

| | Sampling Time (hr) | | | | |
| --- | --- | --- | --- | --- | --- |
| | 18 | 26 | 43 | 50 | DLS(nm) |
| Example 1 (L1:15) | 67 | 107 | 199 | 257 | 211 |
| Example 2 (O1:15) | 53 | 82 | 174 | 221 | 23 |
| Example 3 (L1:15) | 1 | 26 | 84 | 106 | 153 |
| Example 4 (L1:5) | 2 | 31 | 90 | 134 | 207 |
| Example 5 (O1:15) | 4 | 9 | 20 | 29 | 262 |
| Example 6 (O1:5) | 5 | 11 | 24 | 31 | 298 |
| Comparative Example 1 (drug alone) | 3 | 10 | 29 | 37 | — |
| Comparative Example 2 (drug alone) | 0 | 0 | 2 | 3 | — |
| Comparative Example 3 (drug alone) | 0 | 0 | 0 | 0 | — |
| Comparative Example 4 (ER1:15) | 3 | 9 | 13 | 14 | 196 |
| Comparative Example 5 (drug alone) | 6 | 8 | 10 | 12 | — |
| Comparative Example 6 (L1:30) | 32 | 60 | 118 | 159 | 3 |
| Comparative Example 7 (L1:50) | 24 | 40 | 72 | 96 | 3 |
| Comparative Example 8 (ER1:15) | 0 | 11 | 51 | 71 | 9 |
| Comparative Example 9 (ER1:15) | 2 | 4 | 12 | 17 | 247 |

It was found from the results illustrated in FIGS. 2 to 5 that the external preparations of the examples are largely improved in the permeability as compared with the external preparations of the comparative examples.

Besides, it was found from the results illustrated in FIG. 5 that the permeability is improved as the weight of the fatty acid ester is lower as compared with the hydrophilic drug.

It was found from the results illustrated in FIG. 6 that even a core-shell structure cannot be improved in the permeability if the molecular weight is lower than 400 and the water-octanol partition coefficient is lower than −3.0.

REFERENCE SIGNS LIST

1 . . . parafilm
2 . . . skin
3 . . . preparation
4 . . . receptor liquid (pH 7.2 phosphate buffer)
5 . . . stirrer

The invention claimed is:

1. A core-shell structure, comprising:
   a core portion containing a hydrophilic drug having a molecular weight of 416 or more and 1500 or less; and
   a shell portion containing a surfactant,
   wherein the core portion is a solid,
   the hydrophilic drug has a water-octanol partition coefficient of −3 or more and 6 or less,
   the surfactant has an alkyl group or an alkenyl group having 10 to 15 carbon atoms,
   the surfactant is at least one selected from the group consisting of sucrose fatty acid esters, glycerin fatty acid esters, polyoxyethylene glycerin fatty acid esters, sorbitan fatty acid esters, and polyoxyethylene sorbitol fatty acid esters,
   a mass ratio between the hydrophilic drug and the surfactant (hydrophilic drug:surfactant) is 1:5 to 1:20, and
   the core-shell structure is obtained by a method for producing comprising a step of drying a W/O emulsion containing the hydrophilic drug in an aqueous phase.

2. The core-shell structure according to claim 1, wherein the water-octanol partition coefficient of the hydrophilic drug is −3 or more and 4 or less.

3. An external preparation comprising the core-shell structure according to claim 1.

4. A core-shell structure, comprising:
   a core portion containing a hydrophilic drug selected from the group consisting of hydrochlorides and acetates, the hydrophilic drug having a molecular weight of 416 or more and 1500 or less; and
   a shell portion containing a surfactant,
   wherein the core portion is a solid,
   the hydrophilic drug has a water-octanol partition coefficient of −3 or more and 6 or less,
   the surfactant has an alkyl group or an alkenyl group having 10 to 15 carbon atoms,
   the surfactant is at least one selected from the group consisting of sucrose fatty acid esters, glycerin fatty acid esters, polyoxyethylene glycerin fatty acid esters, sorbitan fatty acid esters, and polyoxyethylene sorbitol fatty acid esters,
   a mass ratio between the hydrophilic drug and the surfactant (hydrophilic drug:surfactant) is 1:5 to 1:20, and
   the core-shell structure is obtained by a method for producing comprising a step of drying a W/O emulsion containing the hydrophilic drug in an aqueous phase.

5. The core-shell structure according to claim 1, further comprising an antiseptic selected from the group consisting of methyl parahydroxybenzoate, propyl parahydroxybenzoate, phenoxyethanol, and thymol.

6. The core-shell structure according to claim 5, wherein the antiseptic is contained in the core portion, and a content of the antiseptic in the core portion is 0.01% by mass to 10% by mass.

7. The core-shell structure according to claim 5, wherein the antiseptic is contained in the shell portion, and a content of the antiseptic in the shell portion is 0.01% by mass to 10% by mass.

* * * * *